United States Patent
Hetling et al.

(10) Patent No.: US 10,292,580 B2
(45) Date of Patent: May 21, 2019

(54) PATTERN STIMULUS FOR VISUAL FUNCTION TESTING

(71) Applicant: THE BOARD OF TRUSTEES OF THE UNIVERSITY OF ILLINOIS, Urbana, IL (US)

(72) Inventors: John Hetling, Dyer, IN (US); Zahra Derafshi, Chicago, IL (US); Shresta Patangay, Chicago, IL (US)

(73) Assignee: THE BOARD OF TRUSTEES OF THE UNIVERSITY OF ILLINOIS, Urbana, IL (US)

( * ) Notice: Subject to any disclaimer, the term of this patent is extended or adjusted under 35 U.S.C. 154(b) by 302 days.

(21) Appl. No.: 14/783,618

(22) PCT Filed: Apr. 18, 2014

(86) PCT No.: PCT/US2014/034636
§ 371 (c)(1),
(2) Date: Oct. 9, 2015

(87) PCT Pub. No.: WO2014/172625
PCT Pub. Date: Oct. 23, 2014

(65) Prior Publication Data
US 2016/0081544 A1 Mar. 24, 2016

Related U.S. Application Data

(60) Provisional application No. 61/845,180, filed on Jul. 11, 2013, provisional application No. 61/813,386, filed on Apr. 18, 2013.

(51) Int. Cl.
*A61B 3/024* (2006.01)
*A61B 3/00* (2006.01)
(Continued)

(52) U.S. Cl.
CPC ............... *A61B 3/024* (2013.01); *A61B 3/00* (2013.01); *A61B 3/0008* (2013.01);
(Continued)

(58) Field of Classification Search
CPC ............ A61B 5/16; A61B 3/113; A61B 5/162
(Continued)

(56) References Cited

U.S. PATENT DOCUMENTS 3,574,450 A * 4/1971 White ...................... A61B 3/10
351/222
4,063,807 A 12/1977 Gelius et al.
(Continued)

OTHER PUBLICATIONS

International Search Report and Written Opinion for Application No. PCT/US2014/034636 dated Sep. 25, 2014 (19 pages).

*Primary Examiner* — Daniel L Cerioni
(74) *Attorney, Agent, or Firm* — Michael Best & Friedrich LLP

(57) ABSTRACT

A pattern stimulus system is described that includes a hemispherical concave surface, a plurality of illumination sources, and a controller. The illumination sources are arranged on the hemispherical concave surface in a plurality of annular rows and a plurality of radial columns. The control is configured to operate the illumination sources to display a checkerboard pattern by illuminating a first subset of the illumination sources and dimming a second subset of the illumination sources. The control is further configured to invert the checkerboard pattern by dimming the first subset of the illumination sources and illuminating the second subset of the illumination sources. Methods are also described for using the pattern stimulus system to evaluate a condition of the eye and to diagnose diseases of the eye.

19 Claims, 4 Drawing Sheets

(51) Int. Cl.
*A61B 5/0484* (2006.01)
*A61B 5/0496* (2006.01)
*A61B 5/00* (2006.01)

(52) U.S. Cl.
CPC .......... *A61B 3/0033* (2013.01); *A61B 5/0496* (2013.01); *A61B 5/04842* (2013.01); *A61B 5/7271* (2013.01)

(58) Field of Classification Search
USPC ........................................................ 600/558
See application file for complete search history.

(56) References Cited

U.S. PATENT DOCUMENTS

| | | | |
|---|---|---|---|
| 5,024,519 A | | 6/1991 | Howard et al. |
| 5,835,188 A | | 11/1998 | Moreno |
| 6,022,107 A | | 2/2000 | Kutschbach et al. |
| 6,477,407 B1 | * | 11/2002 | Klistorner .............. A61B 3/024 600/544 |
| 2003/0020875 A1 | | 1/2003 | Sperling |
| 2005/0158687 A1 | * | 7/2005 | Dahm .................. A61C 19/004 433/29 |
| 2007/0052636 A1 | * | 3/2007 | Kalt ........................ G09G 3/34 345/83 |
| 2007/0188710 A1 | * | 8/2007 | Hetling ................ A61B 5/0496 351/221 |
| 2008/0019127 A1 | | 1/2008 | Dick et al. |
| 2011/0051088 A1 | | 3/2011 | Shimizu et al. |
| 2011/0237999 A1 | | 9/2011 | Muller et al. |

\* cited by examiner

PATTERN STIMULUS FOR VISUAL FUNCTION TESTING

CROSS-REFERENCE TO RELATED APPLICATION(S)

This is a U.S. national stage entry of International Patent Application No. PCT/US2014/034636, filed on Apr. 18, 2014, which claims priority to U.S. Provisional Patent Application No. 61/845,180, filed on Jul. 11, 2013, and U.S. Provisional Patent Application No. 61/813,386, filed on Apr. 18, 2013, the entire contents of all of which are fully incorporated herein by reference.

BACKGROUND

The present invention relates generally to a visual stimulation source for electrophysiology and methods of using a visual stimulation source. More specifically, the present invention relates to a device that presents a patterned stimulus to the eye and records a bioelectric signal generated by the retina.

SUMMARY

Existing ERG pattern stimulus sources typically use a conventional flat monitor to present a stimulus pattern to a subject. However, such systems present the stimulus to subject's center visual field. Eye diseases such as glaucoma often first present in the peripheral retina. A vision test system that measures function in the peripheral retina would enhance early detection of such diseases.

In some embodiments, the invention provides a pattern visual stimulus source for electrophysiology. The visual stimulus source includes a patterned stimulus—a checkerboard pattern that inverts at a desired frequency—that is presented to the eye. A bioelectric signal generated by the retina is then recorded from the eye surface (e.g., electroretinogram (ERG)). In other embodiments, the bioelectric signal generated by the brain (i.e, the visual cortext) in response to the visual stimulus is recorded from the scalp (i.e., visually evoked potential (VEP)). This type of stimulus (i.e., an inverted checkerboard) is used to evoke a response that is dominated by the retinal ganglion cells. The response of the retinal ganglion cells is of interest in vision science and clinical diagnosis, especially for glaucoma.

In various embodiments, the checkerboard stimulus pattern is presented to the entire visual field—including the far peripheral visual field. The stimulus source includes a hemispherical screen that fills the entire visual field of the subject. When a subject is positioned in front of the stimulus source and the direction of gaze is fixed on a small target near the center of the concave surface of the hemispherical screen, the subject cannot see past the edges of the screen. As a result, the checkerboard stimulus is presented to the entire anatomical retina without physically contacting the eye or introducing energy (e.g., electrical stimulus) to the body. Instead, some embodiments are entirely non-invasive.

Because eye diseases such as glaucoma often first present in the peripheral retina, a vision test that measures function in the peripheral retina can improve early detection of these diseases. In embodiments that utilize a pattern ERG (pERG), the patterned stimulus evokes a response from ganglion cells in the peripheral retina and can be used to detect/diagnose glaucoma.

In some embodiments, the pERG response is used to measure a psychophysical threshold which tests visual function along the entire visual pathway. In addition to evaluation of glaucoma, these tests can be used to detect/diagnose diseases such as retinitis pigmentosa and idiopathic intracranial hypertension.

In some embodiments, the invention provides a method of stimulating any portion of the visual field with the checkerboard stimulus pattern by restricting the area on the screen over which the checkerboard is visible. The remaining portion of the visual field is filled with darkness or a uniform light level selected by the user (or operator). In this way, the system can be used to probe the peripheral retina sector-by-sector to identify a region of the retina where damage is located (e.g., where disease has presented). In some embodiments, the operator is also able to control the frequency at which the checkerboard inverts as well as the contrast and luminance of the checks of the checkerboard pattern.

In one embodiment, the invention provides a pattern stimulus system comprising a hemispherical concave surface, a plurality of illumination sources, and a controller. The illumination sources are arranged on the hemispherical concave surface in a plurality of annular rows and a plurality of radial columns. The control is configured to operate the illumination sources to display a checkerboard pattern by illuminating a first subset of the illumination sources and dimming a second subset of the illumination sources. The control is further configured to invert the checkerboard pattern by dimming the first subset of the illumination sources and illuminating the second subset of the illumination sources.

Other aspects of the invention will become apparent by consideration of the detailed description and accompanying drawings.

DETAILED DESCRIPTION

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Figure 1A:
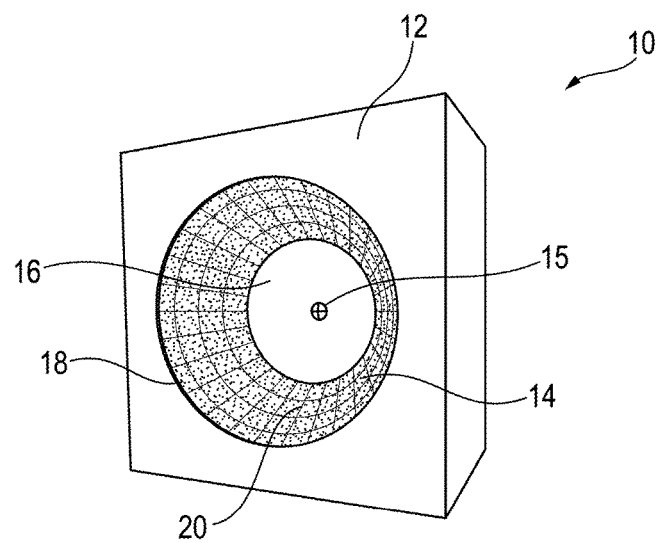
FIG. 1A is a perspective view of the pattern stimulus source.

FIG. 1 shows a pattern stimulus source device 10 including a housing 12, a concave "screen" surface 14, a target 15, a center portion of a hemispherical concave dome 16, and a plurality of illumination sources 18. The concave screen surface 14 and the center portion 16 together form the surface of a hemispherical concave dome. The interior of the concave surface 14 and the target 16 together form a hemispherical dome with a radius equal to the shortest distance of focus for a typical adult—approximately 14 inches for a human eye. The dome in this example is constructed of an acrylic material. However, other constructions may utilize other materials in addition to or instead of acrylic. The concave and convex surfaces of the dome are treated so that they are optically diffused (i.e., "frosted").

The concave screen surface 14 is divided into a checkerboard pattern having thin opaque dividers 20 extending perpendicular to the concave surface 14. Each check of the checkerboard pattern is illuminated by a light-emitting diode (LED) or an array of LEDs (with or without additional diffusing elements) such that the luminance of each check, when viewed from the concave side, is approximately uniform. The opaque dividers 20 are positioned on the back side (i.e., the convex surface) of the concave screen surface 14 to prevent light from each LED from entering the neighboring "checks."

Because of the shape and size of the hemispherical surface, the checkerboard is presented to the entire visual field of a subject—including the far peripheral visual field. As such, when a subject is positioned in front of the pattern stimulus source 10 and the direction of gaze is fixed on the small target 15 near the center of the concave surface of the hemispherical screen, the subject cannot see past the edges of the screen 14. As a result, the checkerboard stimulus pattern is presented to the entire anatomical retina of the subject. As described in further detail below, the LEDs are controlled by a circuit and/or computer program that allows a user to control the luminance and contrast of each check and the frequency of checkerboard inversion (i.e., the rate at which white checks invert to black and black checks invert to white).

The stimulus source device 10 provides a stimulus that is consistent with the standard pattern ERG stimulus recommended by the International Society for Clinical Electrophysiology of Vision (ISCEV), as well as a wide range of additional stimulus parameter values that may be useful for various applications. In particular, the stimulus source device can be configured to provide a luminance of 80 candela per square meter ($cd/m^2$), a contrast of approximately 80%, and an inversion rate of 4 reversals per second.

Figure 1B:
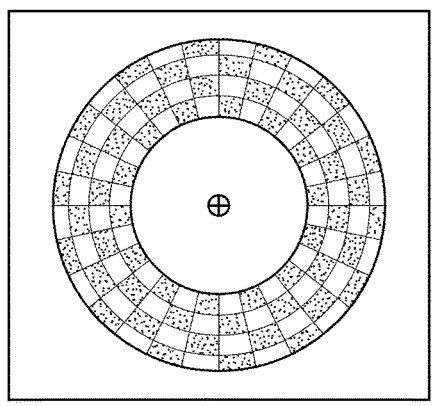
FIG. 1B is an elevation view of the pattern stimulus source of FIG. 1A operating with an inverting checkerboard pattern.

FIG. 1B shows the pattern stimulus source device 10 with the full array of LEDs operating to present the checkerboard pattern. The screen surface 14 provides a checkerboard patterns consisting of four annular rows that fill the far-peripheral visual field. The screen surface also includes 30 radial columns for a total of 120 selectively lighted segments. As shown in FIG. 1B, the center 16 of the hemispherical dome does not illuminate in this example. However, in other constructions, the checkerboard pattern can be extended to cover the entire concave surface of the hemispherical dome.

Figure 1C:
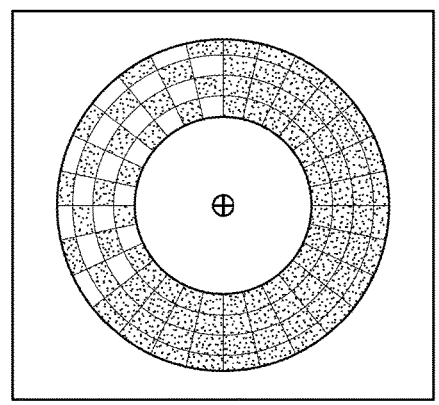
FIG. 1C is an elevation view of the pattern stimulus source of FIG. 1A operating with one-third of the pattern illuminated.

The stimulus source device 10 can also be controlled to selectively stimulate only a portion of the visual field with the checkerboard pattern by restricting the area on the concave surface over which the checkerboard pattern is visible. The remaining portion of the visual field is filled with darkness or a uniform light level selected by the user or a clinician/operator. For example, as shown in FIG. 1C only the upper left third of the checkerboard pattern is illuminated. By selectively applying the stimulus source pattern to only a portion of the visual field, the device can be used to probe the peripheral retina sector-by-sector to identify specific region(s) of the retina where damage is located.

Figure 2C:
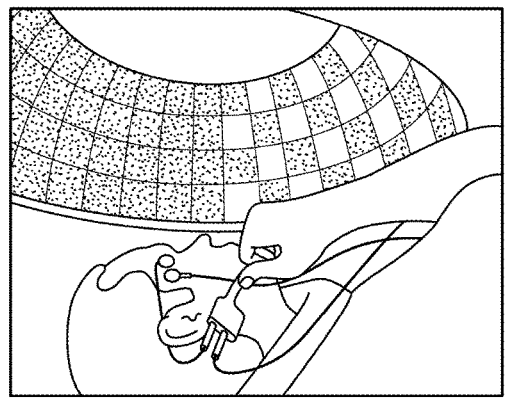
FIG. 2C is a perspective view of the user positioned relative to the pattern stimulus source of FIG. 1A with only a lower left peripheral quadrant checkerboard pattern illuminated.
Figure 2B:
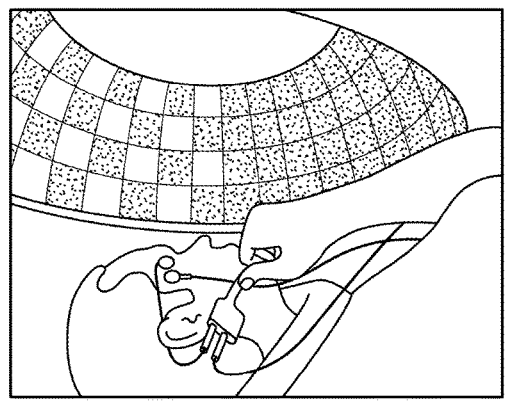
FIG. 2B is a perspective view of the user positioned relative to the pattern stimulus source of FIG. 1A with only an upper left peripheral quadrant checkerboard pattern illuminated.
Figure 2A:
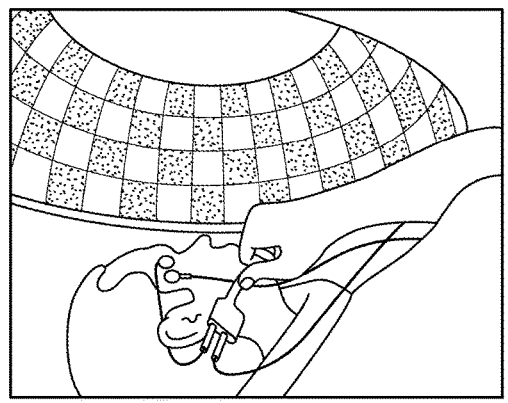
FIG. 2A is a perspective view of a user positioned relative to the pattern stimulus source of FIG. 1A with a full peripheral checkerboard pattern illuminated.

During use, the subject (human or animal) is positioned before the concave side of the dome with the direction of gaze approximately toward the center or apex of the concave surface as illustrated in FIG. 2A. The distance between the user and the center of the concave surface is selected such that the concave surface fills the subject's entire visual field. A recording electrode is placed on the eye or the scalp of the subject to record the subjects response (i.e., via ERG or VEP, respectively). As described in further detail below, the pattern stimulus source is then turned on and the signal recorded continuously for several check transitions (i.e., inversions of the checkerboard pattern). As described above, the system can be configured to present the checkerboard pattern to the entire field of view (as illustrated in FIG. 2A) or only a portion of the field of view (as illustrated in FIGS. 2B and 2C).

Figure 3:
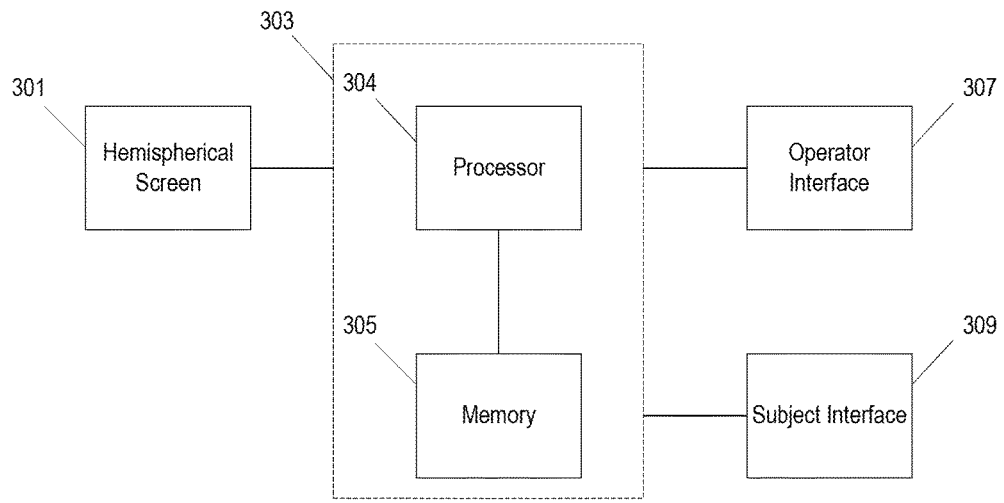
FIG. 3 is a block diagram of a pattern stimulus system including the pattern stimulus source of FIG. 1A.

FIG. 3 illustrates the various components coupled to the stimulus source device in order to provide for operation of the system. The hemispherical screen 301 is coupled to a controller 303. The controller 303 in this example includes a processor 304 and a non-transitory computer-readable memory 305. The memory 305 stores instructions that are executed by the processor 304 to control the operation of the controller 303. In various constructions, the controller 303 can also include additional circuitry (not pictured) to selectively provide power to each LED in the array (e.g., a pulse generator and LED array driver circuit). The controller 303 may also include an amplifier and filter component to receive a response signal from the electrode(s) applied to the user and to convert the response signal to a digital signal that can be analyzed.

In various other constructions, the individual components of the control 303 discussed above can be incorporated into a single device housing or can be divided into multiple different components. For example, the processor 304 and memory 305 can be fitted into the same housing as the hemispherical screen 301 while the amplifier/filter components are implemented as a separate signal processing unit. Furthermore, although the controller 303 is described in this example as including a processor 304 and memory 305, in other constructions, the controller 303 may be implemented in another form such as, for example, an application specific integrated circuit (ASIC).

The controller 303 is coupled to an operator interface 307 and a subject interface 309. In the examples described below, the operator interface 307 is implemented as a graphical user interface shown on the screen of a desktop computer system. However, in other constructions, the operator interface 307 can be implemented as a separate stand-alone device or integrated into the same housing as the hemispherical screen 301. Furthermore, in the examples below, the subject interface 309 includes a button that is activated by the subject in response to the test stimulus or as an electrode attached to the subject's head or eye. However, in other constructions, the subject interface 309 can take other forms. For example, the subject interface 309 may be implemented on the same desktop computer system as the operator interface 307 as a graphical user interface that provides information to the subject before and after the test procedure. In such constructions, the test subject might click a button of the mouse or a key on the keyboard to indicate that the pattern is perceived.

Figure 4:
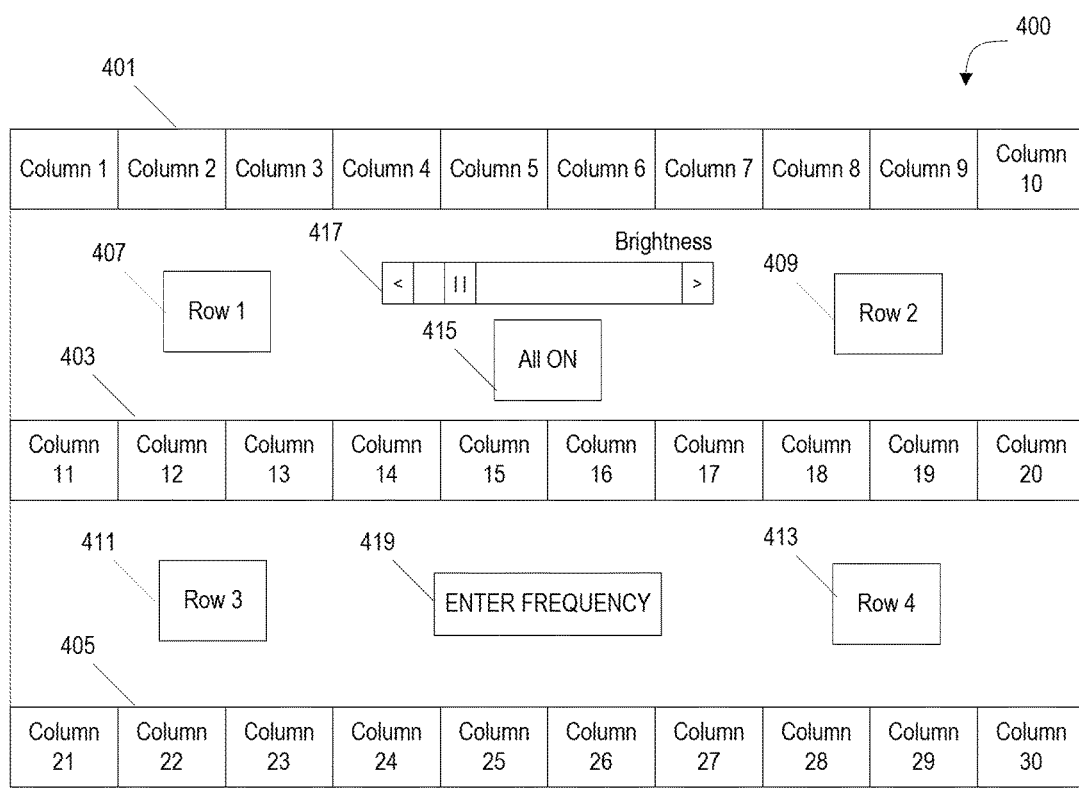
FIG. 4 is a graphical user interface used for operating the pattern stimulus source of FIG. 1A.

FIG. 4 illustrates one example of a graphical user interface 400 that can be implemented as the operator interface 307. The graphical user interface 400 includes three series of buttons 401, 403, and 405, each including ten individually selectable buttons. Each button corresponds to a specific column of the LED array of the hemispherical screen. When a "column" button is selected, the checkerboard pattern is displayed using the corresponding LED column. When the column button is deselected, the checkerboard pattern is not presented on the corresponding column. Instead all LEDs in the corresponding column will remain either dark or lighted at the defined light level.

In the example of FIG. 4, the LED column buttons are arranged into three groups 401, 403, and 405. This arrangement allows the operator to easily select a specific one, two, or three section(s) of the hemispherical dome to display the checkerboard pattern. In other constructions, the LED column buttons can be arranged differently to provide a different meaningful grouping of columns (for example, four groups each corresponding to a specific quadrant of the hemispherical dome). However, it is noted that each individual column button can be selected separately from the other columns in the group. As such, the operator is free to select any combination of columns to be used during the test procedure.

The user interface 400 also includes four "ROW" buttons 407, 409, 411, and 413. Like the "COLUMN" buttons described above, each ROW button controls whether a corresponding annular row of LEDs is used to display the checkerboard pattern or whether the annular row of LEDs will remain dark (or lighted at a static level). Furthermore, an "All ON" button 415 is included such that, when selected, all "COLUMN" buttons and all "ROW" buttons are also selected. In some constructions, the "All ON" button 415 can also be used before or after a test procedure to verify whether all of the LEDs are operating properly—when the "All ON" button 415 is selected, all of the LEDs turn on; when the "All ON" button 415 is deselected, the LEDs turn off.

The user interface 400 also includes a brightness slider bar 417 to define the level of brightness/luminance of the LED array. A text box 419 is used to set the frequency at which the checkerboard pattern is inverted. However, in other constructions, the text box 419 can be replaced by a drop-down box or a slider bar that can be used to define the inversion frequency.

Figure 5:
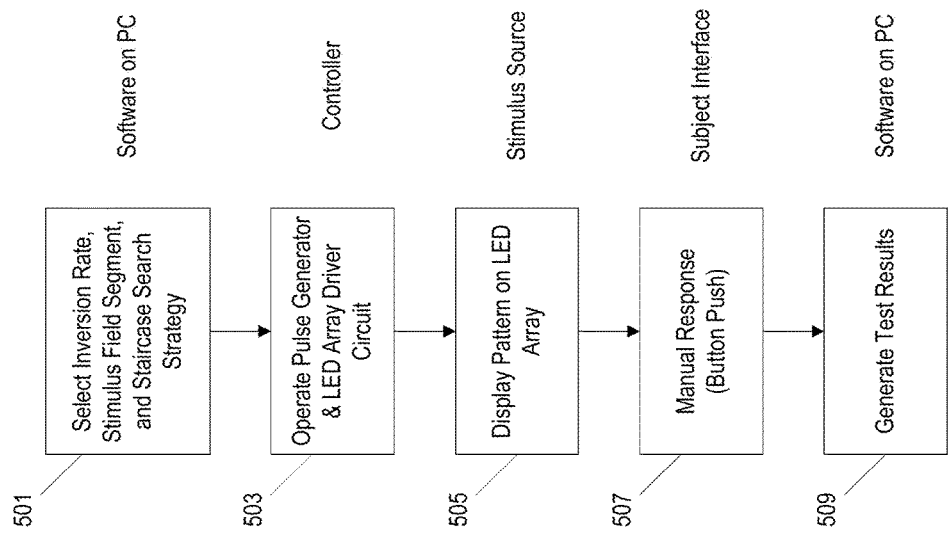
FIG. 5 is a flowchart of a method of using the pattern stimulus system of FIG. 2 for peripheral threshold testing.

FIG. 5 illustrates a method of using the system described above for measuring visual function by probing the peripheral retina. As described above, the operator can use the graphical user interface of FIG. 4 to define various parameters for the test including the inversion rate and the size/location of the stimulus field (step 501). The user interface can also be used to define a "staircase" search strategy that changes the brightness of the checks and the subset of checks that are activated throughout the course of a testing procedure.

Once the test parameters are defined (step 501), the controller implements a clock pulse generator that times the operation of an LED driver circuit (step 503). In response, the pattern is displayed on the hemispherical dome (step 505). As the visual stimulus is displayed and changed, the subject operated a subject interface (i.e., a manually pressed button) to indicate when the subject is able to perceive the stimulus pattern (step 507). Once the test subject provides the manual response, the method continues according to the defined staircase search strategy until the brightness threshold for perception is determined for each subset of checks (i.e., each small area of the testing subject's visual field).

An example of one "staircase" search strategy would be to activate a defined subset of checks at a given brightness—for example, the checks positioned in rows 1 and 2 and in columns 1 and 2. If the activated checks are perceived by the testing subject (as indicated by a button press), then the brightness is lowered by a set amount. If the activated checks are still perceived at the lower brightness level, the brightness is lowered again. If the activated checks are not perceived at a given brightness, the brightness is increased in smaller increments. This process is repeated—while concurrently changing the location (i.e., subset) of activated checks—until the brightness threshold for perception is determined in each area of the test subject's visual field.

After the test is complete, the desktop computer system analyzes the timing of the manual response input and generates test results (step 509). The test results include topographic information about the ability of the subject to sense stimulus (i.e., based on when the button was pressed and when it wasn't). These results provide information regarding the function of the visual pathway and are relevant to the diagnosis and monitoring of diseases such as retinitis pigmentosa and idiopathic intracranial hypertension.

Figure 6:
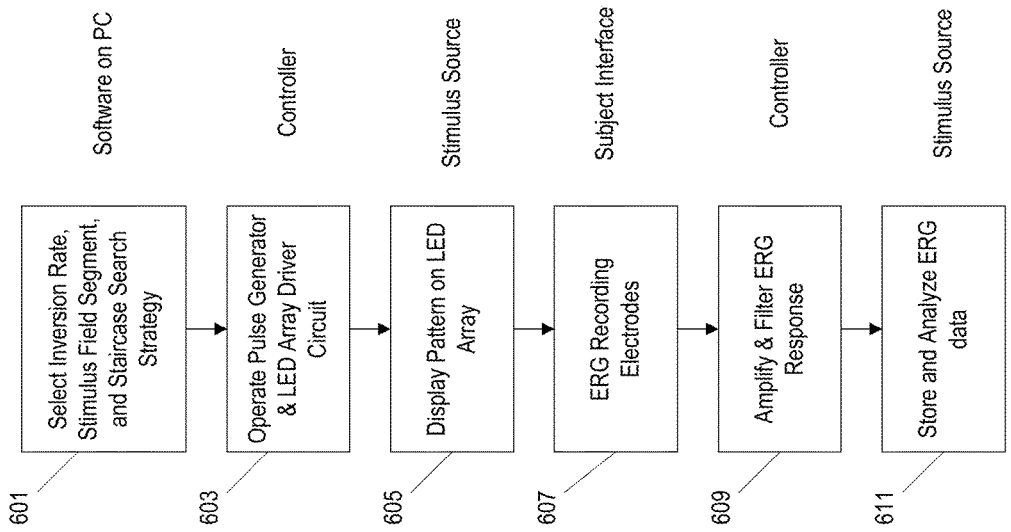
FIG. 6 is a flowchart of a method of using the pattern stimulus system of FIG. 2 for peripheral pattern ERG recording.

FIG. 6 illustrates another method of using the system for measuring and evaluating visual function of a user. In this example, the "push-button" subject interface is replaced by an electrode that is placed on the subject's eye. The electrode signal, in response to the visual stimulus, is processed to present an ERG data record for the subject. Again, the operator uses the operator interface to define various parameters for the test procedure (step 601). The controller then initiates a pulse generator/clock and operates the LED array driver circuit based on the defined parameters (step 603). As a result, the stimulus pattern is displayed on the hemispherical screen (step 607).

The electrode detects the subject's response to the stimulus and provides an ERG signal (step 607) which is amplified and filtered by the controller (step 609). The amplified, filtered ERG signal is converted to a digital signal which is stored to the memory of the controller (or an attached computer) (step 611). The stored ERG signal is then analyzed. For example, window data may be timed to the pattern inversion. A running average response can be calculated in real-time and waveform analysis can be performed on the stored data. The output waveforms provide information that is relevant to the response of the retinal ganglion cells and is of interest in vision science and clinical diagnosis—particularly for the early diagnosis of glaucoma.

The systems and methods described above provide an electrophysiological and psychophysical visual testing system configured to probe the peripheral retina using a hemispherical pattern stimulus source. The hemispherical pattern stimulus source can be used in conjunction with manually activated peripheral threshold testing or with peripheral pattern ERG recording. Software is then used to collect and analyze data indicative of the peripheral retina response. Various features and advantages of the invention are set forth in the following claims.

What is claimed is:

1. A pattern stimulus system comprising:
   a hemispherical concave surface;
   a plurality of illumination sources arranged on the hemispherical concave surface in a plurality of annular rows and a plurality of radial columns; and
   a controller configured to operate the illumination sources to
     display a checkerboard pattern on the hemispherical concave surface by illuminating a first subset of the illumination sources and dimming a second subset of the illumination sources, wherein the hemispherical concave surface is configured to display the checkerboard pattern extending beyond a far peripheral visual field of a testing subject; and
     inverting the checkerboard pattern displayed on the hemispherical concave surface by dimming the first subset of the illumination sources and illuminating the second subset of the illumination sources.

2. The pattern stimulus system of claim 1, further comprising a plurality of opaque dividers positioned on a backside hemispherical convex surface extending perpendicular to the concave surface and arranged to separate individual illumination sources of the plurality of illumination sources.

3. The pattern stimulus system of claim 1, wherein the hemispherical concave surface is sized to include a radius that is greater than or equal to a shortest distance of focus for a typical adult eye.

4. The pattern stimulus system of claim 1, wherein the hemispherical concave surface is sized to include a radius that is greater than or equal to 14 inches.

5. The pattern stimulus system of claim 1, wherein each illumination source of the plurality of illumination sources includes a light emitting diode.

6. The pattern stimulus system of claim 1, wherein each illumination source of the plurality of illumination sources includes an array of light emitting diodes.

7. The pattern stimulus system of claim 1, further comprising a processor and a non-transient computer-readable memory storing instructions that, when executed by the processor, cause the pattern stimulus system to invert the checkerboard pattern at a defined frequency.

8. The pattern stimulus system of claim 7, further comprising a user interface configured to receive an input indicative of the defined frequency from a user.

9. The pattern stimulus system of claim 1, further comprising a processor and a non-transient computer-readable memory storing instructions that, when executed by the processor, cause the pattern stimulus system to display the checkerboard pattern to a portion of a testing subject's visual field by
   illuminating only the illumination sources of the first subset of illumination sources that correspond to a defined plurality of radial columns and a defined plurality of annular rows and
   dimming only the illumination source of the first subset of illumination sources that correspond to the defined plurality of radial columns and the defined plurality of annular rows.

10. The pattern stimulus system of claim 9, wherein the instructions, when executed by the processor, cause the pattern stimulus system to change a quantity and a location of the defined plurality of radial columns and the defined plurality of annular rows over time during a vision test.

11. The pattern stimulus system of claim 10, further comprising a user input device, and wherein the instructions, when executed by the processor, cause the pattern stimulus system to monitor an input signal from the user input device, wherein the input signal is indicative of manual confirmation from the testing subject that the checkerboard pattern is perceived.

12. The pattern stimulus system of claim 11, wherein the instructions, when executed by the processor, cause the pattern stimulus system to
   correlate the input signal from the user input device to a corresponding quantity and location of the defined plurality of radial columns and the defined plurality of annular rows, and
   identify a location of eye damage based on the correlation.

13. The pattern stimulus system of claim 12, wherein the location of eye damage is identified based on identified locations on the hemispherical concave surface where the checkerboard pattern was displayed and was not perceived by the testing subject.

14. The pattern stimulus system of claim 10, wherein the instructions, when executed by the processor, cause the pattern stimulus system to
   receive a signal from an electrode indicative of a pattern electroretinogram response of the testing subject to the displayed checkerboard pattern,
   correlate the signal from the electrode to a corresponding quantity and location of the defined plurality of radial columns and the defined plurality of annular rows, and
   identify a location of eye damage based on the correlation.

15. The pattern stimulus system of claim 9, wherein the instructions, when executed by the processor, cause the pattern stimulus system to receive a signal from an electrode attached to a surface of an eye of the testing subject, wherein the signal is indicative of a pattern electroretinogram response of the testing subject to the displayed checkerboard pattern.

16. The pattern stimulus system of claim 9, wherein the instructions, when executed by the processor, cause the pattern stimulus system to receive a signal from an electrode attached to a location on a head of the testing subject, wherein the signal is indicative of a visually evoked potential response of the testing subject to the displayed checkerboard pattern.

17. The pattern stimulus system of claim 1, further comprising:
   an electrode selectively attachable to a surface on a testing subject;
   a processor; and
   a non-transient computer-readable memory storing instructions that, when executed by the processor, cause the pattern stimulus system to receive a signal from the electrode indicative of a response of the testing subject to the displayed checkerboard pattern.

18. A method of operating a pattern stimulus system for visual function testing, the method comprising:
   positioning a head of a testing subject proximate to a hemispherical concave surface of the pattern stimulus system;
   displaying a checkerboard pattern on the hemispherical concave surface while the gaze of the testing subject is fixed on a small target at or near the center of the hemispherical concave surface such that the checkerboard pattern displayed on the hemispherical concave surface extends beyond a far peripheral visual field of the testing subject; and
   inverting the checkerboard pattern by dimming the first subset of illumination sources and illuminating the second subset of illumination sources.

19. The method of claim 18, further comprising:
adjusting a quantity and a location of a defined plurality of radial columns and a defined plurality of annular rows in the checkerboard patterns that are displayed on the hemispherical concave surface over time;
receiving a signal from an electrode attached to the testing subject, the signal being indicative of a pattern electroretinogram response of the testing subject to the displayed checkerboard pattern;
correlating the signal from the electrode to a corresponding quantity and location of the defined plurality of radial columns and the defined plurality of annular rows displayed on the hemispherical concave surface; and
identifying a location of eye damage of the testing subject based on the correlation.

* * * * *